United States Patent [19]
Meathrel et al.

[11] Patent Number: 5,833,622
[45] Date of Patent: *Nov. 10, 1998

[54] NON-INVASIVE FETAL PROBE HAVING IMPROVED MECHANICAL AND ELECTRICAL PROPERTIES

[75] Inventors: William G. Meathrel, Getzville; Ignaty Gusakov, East Aurora, both of N.Y.; Mohammed Saleem, Grananoque; Shirley A. Binks, Ontario, both of Canada

[73] Assignee: Graphic Controls Corporation, Buffalo, N.Y.

[ * ] Notice: The term of this patent shall not extend beyond the expiration date of Pat. No. 5,474,065.

[21] Appl. No.: 741,942

[22] Filed: Oct. 31, 1996

Related U.S. Application Data

[63] Continuation-in-part of Ser. No. 487,806, Jun. 7, 1995, Pat. No. 5,665,477, which is a continuation-in-part of Ser. No. 222,729, Apr. 4, 1994, Pat. No. 5,474,056.

[51] Int. Cl.$^6$ .................................. A61B 5/0444
[52] U.S. Cl. .......................... 600/511; 600/376
[58] Field of Search .................... 128/639–643, 128/698; 607/138, 149, 152, 153; 252/500, 521; 424/78.31, 78.35, 78.37, 443, 447; 600/511, 376

[56] References Cited

U.S. PATENT DOCUMENTS

| | | |
|---|---|---|
| Re. 28,990 | 10/1976 | Hon et al. . |
| 3,590,810 | 7/1971 | Kopecky . |
| 3,750,650 | 8/1973 | Ruttgers . |

(List continued on next page.)

FOREIGN PATENT DOCUMENTS

| | | |
|---|---|---|
| 1103761 | 6/1981 | Canada . |
| 0099077 | 1/1984 | European Pat. Off. . |
| 0137500 | 4/1985 | European Pat. Off. . |
| 0248627 | 12/1987 | European Pat. Off. . |
| 0442011 | 8/1991 | European Pat. Off. . |
| 676170 | 11/1995 | European Pat. Off. ...... A61B 5/0448 |

(List continued on next page.)

OTHER PUBLICATIONS

N.J. Randall et al., Detection of the Fetal ECG During Labour by an Intrauterine Probe, 27th Annual Meeting of Biological Eng. Society, Oxford, UK, 2–4 Sep. 1987.
Okane et al., Non–invasive Continuous Fetal Transcutaneous $pO_2$ and $pCO_2$ Monitoring During Labor, J. Pernat. Med 17 (1989), pp. 399–410.
Schmidt, Glue Fixation of the $tcPco_2$ Electrode for Fetal Monitoring, J. Perinat. Med 15 (1987), pp. 377–382.
Hofmeyr et al., A Nonpenetrating Fetal Scalp Electrode, British Journal of Obstetrics and Gynaecology, vol. 100, pp. 649–652 (Jul. 1993).
A.M. Gulmezoglu et al., Randomised Evaluation of a Prototype Suction Fetal Scalp Electrode, British Journal of Obstetrics and Gynacology, vol. 103, pp. 513–517 (Jun. 1996).
European Search Report dated Aug. 4, 1995.
European Search Report Dated Feb. 19, 1998.

*Primary Examiner*—Jeffrey R. Jastrzab
*Attorney, Agent, or Firm*—Ratner & Prestia

[57] ABSTRACT

A non-invasive fetal probe having enhanced adhesion and electrical isolation for attaching to the presenting part of a fetus and sensing at least one fetal parameter during labor and delivery. In one embodiment of the present invention, the electrical isolation of the fetal probe includes a non-conductive element used in combination with various conductive assemblies made from gel formulations which are polymerized to form a fetal sensor. The non-conductive element in addition to providing physical separation also enhances electrical separation between fetal and maternal sensing elements of the fetal probe. Non-invasive fetal probes having low-profile designs are also provided which help decrease the tendency of the fetal probes to detach caused by forces generated upon the probe by the head of the fetus, the cervix of the mother, or both.

38 Claims, 11 Drawing Sheets

U.S. PATENT DOCUMENTS

| | | |
|---|---|---|
| 3,827,428 | 8/1974 | Hon et al. . |
| 3,910,271 | 10/1975 | Neward . |
| 3,958,564 | 5/1976 | Langguth . |
| 4,149,528 | 4/1979 | Murphy . |
| 4,180,080 | 12/1979 | Murphy . |
| 4,299,232 | 11/1981 | Zilanti . |
| 4,301,806 | 11/1981 | Helfer . |
| 4,308,873 | 1/1982 | Maynard . |
| 4,314,044 | 2/1982 | Hughes et al. ............................ 524/808 |
| 4,320,764 | 3/1982 | Hon . |
| 4,437,467 | 3/1984 | Helfer et al. . |
| 4,458,695 | 7/1984 | Larimore . |
| 4,469,105 | 9/1984 | Staver . |
| 4,515,162 | 5/1985 | Yamamoto . |
| 4,577,635 | 3/1986 | Meredith . |
| 4,602,640 | 7/1986 | Wada et al. . |
| 4,646,747 | 3/1987 | Lundback . |
| 4,658,825 | 4/1987 | Hochberg et al. . |
| 4,706,680 | 11/1987 | Keusch et al. . |
| 4,731,078 | 3/1988 | Stoy et al. . |
| 4,736,749 | 4/1988 | Lundback . |
| 4,825,879 | 5/1989 | Tan et al. . |
| 4,921,904 | 5/1990 | Sparapany et al. . |
| 4,934,371 | 6/1990 | Malis et al. . |
| 4,938,218 | 7/1990 | Goodman et al. . |
| 4,956,170 | 9/1990 | Lee ........................................ 514/772.1 |
| 4,989,607 | 2/1991 | Keusch et al. . |
| 5,002,792 | 3/1991 | Vegoe . |
| 5,025,787 | 6/1991 | Sutherland et al. . |
| 5,109,849 | 5/1992 | Goodman et al. ....................... 128/698 |
| 5,124,076 | 6/1992 | Smuckler . |
| 5,124,107 | 6/1992 | Schmid .................................... 264/255 |
| 5,139,023 | 8/1992 | Stanley et al. . |
| 5,143,071 | 9/1992 | Keusch et al. . |
| 5,154,175 | 10/1992 | Gunther . |
| 5,183,599 | 2/1993 | Smuckler . |
| 5,183,841 | 2/1993 | Bernard ................................... 524/272 |
| 5,184,619 | 2/1993 | Austin . |
| 5,188,108 | 2/1993 | Secker . |
| 5,217,013 | 6/1993 | Lewis et al. . |
| 5,224,478 | 7/1993 | Sakai et al. . |
| 5,247,932 | 9/1993 | Chung et al. ........................... 128/642 |
| 5,254,338 | 10/1993 | Sakai et al. . |
| 5,345,935 | 9/1994 | Hirsch et al. . |
| 5,377,673 | 1/1995 | Van Dell et al. ....................... 128/633 |
| 5,474,065 | 12/1995 | Meathrel et al. ....................... 128/698 |

FOREIGN PATENT DOCUMENTS

| | | |
|---|---|---|
| 2569976 | 3/1986 | France ..................................... 128/612 |
| 2152808 | 4/1973 | Germany ............................... 128/612 |
| 3446115 | 6/1986 | Germany . |
| 3816190 | 8/1989 | Germany ............................... 128/612 |
| 9316259 U | 3/1994 | Germany . |
| P4304693.2 | 8/1994 | Germany . |
| 2 274 995 | 8/1994 | United Kingdom . |
| 90/04352 | 5/1990 | WIPO . |
| 91/07910 | 6/1991 | WIPO . |
| 91/15996 | 10/1991 | WIPO . |
| 92/04864 | 4/1992 | WIPO . |

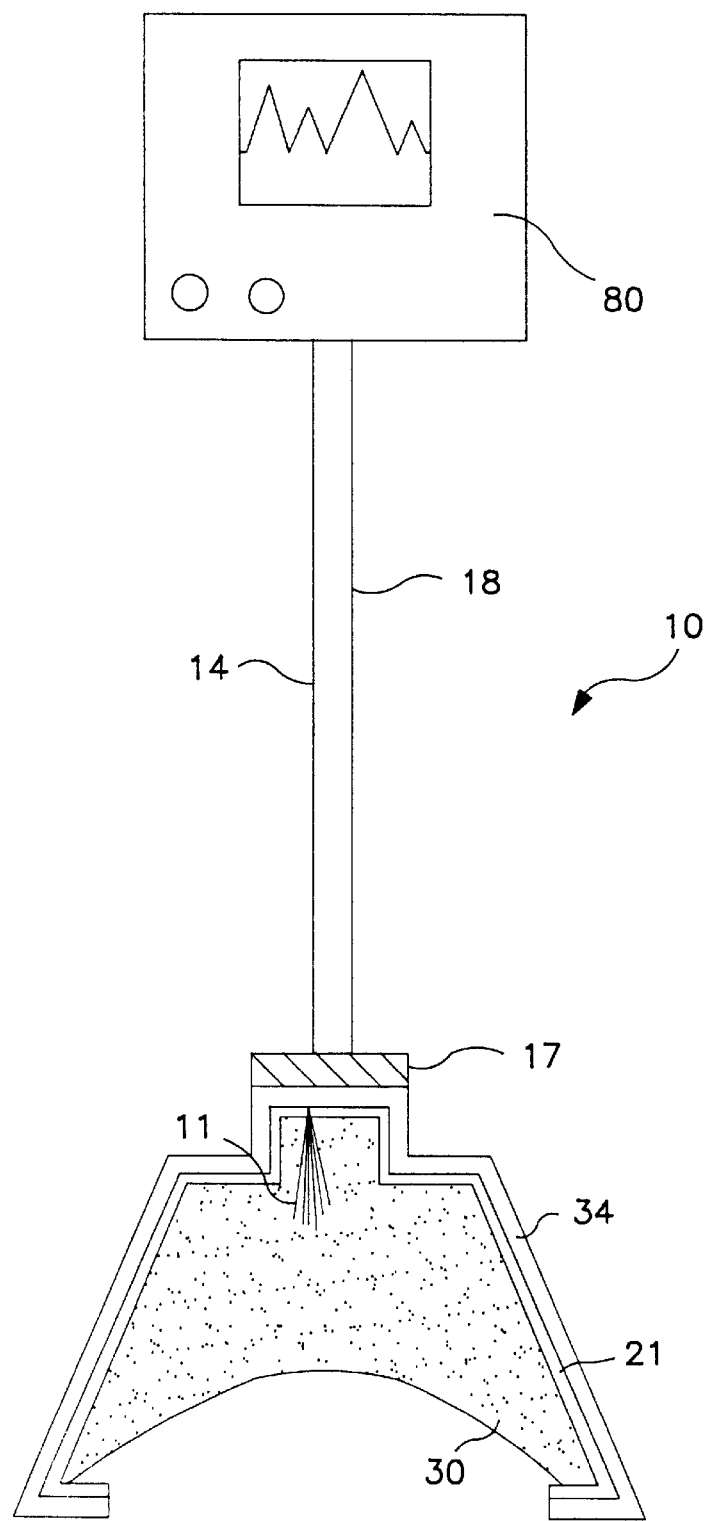
FIG. IA

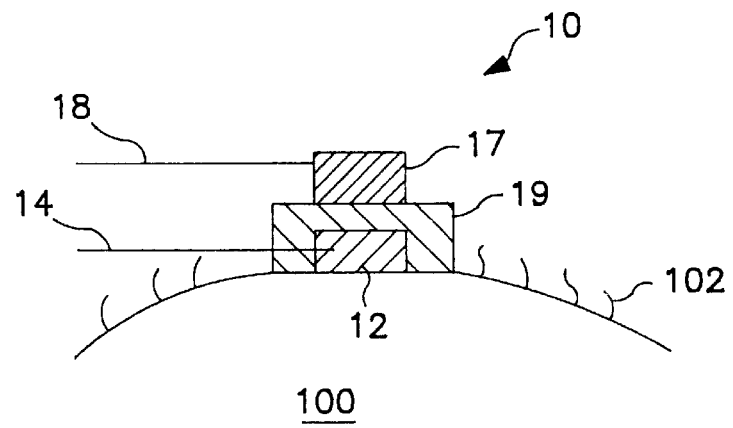
FIG. 23
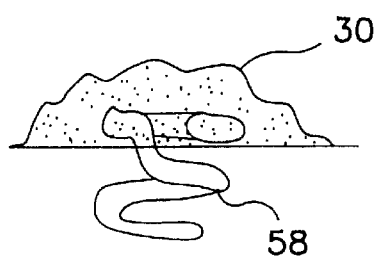 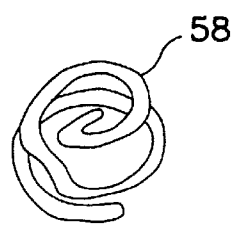 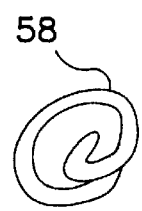
FIG. 24A  FIG. 24B  FIG. 24C

NON-INVASIVE FETAL PROBE HAVING IMPROVED MECHANICAL AND ELECTRICAL PROPERTIES

RELATED APPLICATIONS

This is a continuation-in-part of application Ser. No. 08/487,806 filed on Jun. 7, 1995, now U.S. Pat. No. 5,665,477 which is a continuation-in-part of application Ser. No. 08/222,729 filed on Apr. 4, 1994, now U.S. Pat. No. 5,474,065.

FIELD OF THE INVENTION

The present invention relates to fetal monitoring probes and, more particularly, to a non-invasive fetal probe which adheres biomedical sensors to the skin of a fetus during labor and delivery.

BACKGROUND OF THE INVENTION

During labor and delivery, the well-being of the fetus must be carefully monitored. The procedure of monitoring the fetus allows the clinician to assess the health of the fetus, detect fetal stress, and provide appropriate treatment. Both internal (or direct) and external devices and methods are used to monitor and record such fetal parameters as heart rate, blood gas composition, and pH levels during labor and delivery. Typical internal and external techniques are briefly outlined below and discussed in greater detail in the background section of U.S. Pat. No. 5,474,065.

A. External Methods—Fetal Heart Rate

Several forms of external methods can be used to monitor fetal heart rate. For example, one external method includes the use of ultrasound. Another external method includes the use of a phonotransducer. This method involves placing a microphone, able to detect sound waves generated by the fetal heart, on the mother's abdomen. Abdominal wall electrocardiography is a third type of external fetal heart rate monitoring. All of the external methods of measuring fetal heart rate have an important advantage: they are non-invasive. Consequently, these methods largely avoid adverse effects on the mother or the fetus. The quality of the fetal heart rate recording which uses an external monitoring method is not as good, however, as that achieved by direct methods. This is a major limitation on external monitoring methods. As a general rule, it is necessary to restrict the mother's movements during external monitoring methods to reduce extraneous signals and interferences to obtain accurate tracings. Motion artifact is so common with external techniques that it is virtually impossible to obtain readable tracings unless data processing is used. Valuable information about fetal heart rate variability may be lost through such processing.

B. Direct Methods—Fetal Heart Rate

In direct fetal heart rate monitoring, an electrode is attached directly to the fetal presenting part. Typically, the electrode is a spiral wire or hook which penetrates (is inserted directly into) the fetal epidermis and holds the fetal probe in position. The primary advantage of a direct monitoring system of this kind is that the electrode detects the fetal cardiac electrical signal without the interference which occurs when detecting the signal through another medium such as the mother's abdomen. The fetal cardiac electrical signal is a precise signal, allowing for accurate assessment of the fetal heart rate and any variations in that rate. Further, during direct fetal heart rate monitoring, maternal movement is less restricted without compromising the tracing.

The limitation on this direct fetal heart rate monitoring method is that it is an invasive technique, exposing the mother and the fetus to the potential of injury, infection, or both. Injury may take the form of trauma (such as hemorrhage at the attachment site) to the skin, face, eyes, or other parts of the fetus. In addition, invasive attachment can threaten the life of the fetus by exposing the fetus to maternal body fluids containing infectious components. Venereal diseases and viruses such as acquired immune deficiency (AIDS) and hepatitis B can be transferred directly to the fetus. Moreover, the sharp wire or hook exposes the patient (mother) and clinician to potential injury.

C. Non-Invasive Direct Methods

Various techniques have been described attempting to obtain the benefits of direct fetal monitoring while avoiding the risks related to invasive penetration of the fetal epidermis. Fetal blood gas analysis has been used to assess fetal health during labor. Blood gas analysis is typically done in a clinical laboratory on blood drawn from the fetus during labor (clearly an invasive technique). Alternatively, Okane et al., "Non-invasive continuous fetal transcutaneous $pO_2$ and $pCO_2$ monitoring during labor," Journal Perinatal Medicine, 17(6), 399 (1989), describe non-invasive continuous fetal transcutaneous $pO_2$ and $PCO_2$ monitoring during labor. Okane et al. used a commercially available device, the Micro Gas 7640 probe, available from Kontron Incorporated of Everett, Mass. This probe is fixed to the fetal head using a suction ring connected to a vacuum pump which maintains a negative pressure of 200–300 mm Hg. The sensor is large and requires cervical dilation of 4 cm or more before insertion is possible. The large size of the sensor and the need to apply continuous suction, through an attached vacuum line, are deterrents to the use of the sensor.

Glue fixation of a transcutaneous $pCO_2$ electrode for fetal monitoring has been described by S. Schmidt, "Glue fixation of the $tcPco_2$ electrode for fetal monitoring," Journal Perinatal Medicine, 15(4), 377 (1987). Glue fixation to a fetus is difficult to achieve. It requires sufficient dilation and careful preparation of the attachment site. The electrode often becomes detached during use and may need to be reapplied. In addition, trauma to the skin during removal of a sensor attached by glue is possible. Similarly, pressure-sensitive adhesives such as those used for self-adhesive bandages are hydrophobic and will not adhere to wet surfaces such as fetal skin.

Another non-invasive technique for detecting fetal ECG during labor is described by N. Randall et al., "Detection of the fetal ECG during labour by an intrauterine probe," Journal Biomedicine, (10), 159 (England 1988), and in U.S. Pat. No. 5,025,787 issued to Sutherland et al. The article and patent describe an intrauterine pressure catheter equipped with stainless steel tips which form a multi-point electrode. The intrauterine probe is inserted through the vagina into the uterine cavity. The sensors are held in contact with (but do not adhere to) the fetus by the pressure between the uterus and the fetus. The electronic signal from the sensors is processed to obtain a fetal ECG. The presence of amniotic fluid attenuates the signal from the sensors. The article points out the difficulties in obtaining accurate results due to problems with positioning the electrode tips accurately. Moreover, a degree of electrode isolation is required for optimum detection of fetal signals.

International Patent Publication Number WO 92/04864 (which claims priority of U.K. Patent Applications Number 90-20983 and Number 90-25758 by Van der Merwe) describes a fetal probe with a rigid suction cap approximately 1.5 to 2 cm in diameter. The probe incorporates a fetal heart rate sensor. A negative pressure is created in the rigid cap, by the action of a detachable piston pump, to hold the probe on the fetal skin. The pump is detached after a valve in the cap is closed. The rigid construction of the suction cap and the loss of negative pressure between the fetal skin and suction cap allow the probe to be easily detached during use.

U.S. Pat. No. 5,184,619 issued to Austin describes an intrauterine pressure and fetal heart rate sensor which is inserted between a fetus and the internal uterine wall following rupture of the membranes. The tubular device uses ECG electrodes as well as a pressure transducer to detect fetal heart rate and intrauterine pressure, respectively. Fetal heart rate is detected through the amniotic fluid.

U.S. Pat. No. 5,345,935 issued to Hirsch describes a non-invasive medical probe including a resilient walled suction cup having a peripheral rim for application to a patient's skin. The suction cup is connected to a pump which draws a vacuum inside the cup to adhere the cup to the surface of the patient's skin. Two monitoring electrodes are provided, one centrally within and the other externally adjacent to the cup, which can be used to monitor the heart beat of a fetus.

U.S. Pat. No. 5,474,065 issued to Meathrel et al., which issued from U.S. patent application Ser. No. 07/222,729, provides a non-invasive fetal probe which overcomes the shortcomings of the external devices; the invasive, direct devices; and the non-invasive, direct devices used to measure fetal parameters during labor and delivery. The probe includes a conductive hydrogel which is adhesive to both wet and dry surfaces and is either formed into a suction cup shape or is coated on the inside surface of a suction cup shell. The combination of both the suction cup shape, which initially holds the probe to the fetus, and the hydrogel material, which allows for increased adhesion in the wet environment, enables the probe to be securely attached to the fetus during labor and delivery. Thus, the fetal probe attaches securely to the presenting part of the fetus in a non-invasive manner to ensure attachment without risk of injury to the fetus, mother, or attending personnel. As a result, the probe is able to transmit a clear, unattenuated signal representative of the fetal parameter being monitored.

The non-invasive fetal probes shown in the '065 patent can include various carrier shell configurations to achieve physical or mechanical separation between the maternal fluids and the hydrogel. FIGS. 8A, 8B, and 8C show three examples of variations in the configuration of wall 50 of shell 34. Although the various shell configurations disclosed in the '065 patent help to physically isolate the hydrogel from external fluids, under certain conditions (e.g., in exceptionally wet environments) the maternal and fetal sensing elements of the fetal probe may come in electrical contact. This contact could interfere with detecting an accurate fetal signal (i.e., the differential signal obtained between the maternal (reference) electrode and the fetal electrode) despite the physical separation provided by the shell configurations disclosed.

SUMMARY OF THE INVENTION

The present invention provides an improved non-invasive fetal probe which adheres biomedical sensors to the skin of a fetus during labor. The invention includes electrical and mechanical improvements to provide enhanced adhesion and electrical isolation of non-invasive fetal probes.

In one embodiment of the present invention, the electrical isolation of the fetal probes includes a non-conductive element used in combination with various conductive assemblies made from gel formulations which are polymerized to form a fetal sensor area. It is the incorporation of the non-conductive element which, in addition to providing physical separation, also enhances electrical separation between fetal and maternal sensing elements of the fetal probe.

In another embodiment of the present invention, fetal probes having low-profile designs are provided. These designs help decrease the tendency of the fetal probes to detach caused by forces generated upon the probe by the head of the fetus, the cervix of the mother, or both. This enables the non-invasive probe to be securely attached to the fetus during labor and delivery.

Thus, important aspects of the present invention are the electrical and physical isolation of the maternal and fetal sensing elements. Another aspect of the present invention is to enhance signal separation by increasing the pathway between the maternal and fetal sensing elements. An additional aspect is the use of a low-profile design which allows for a more secure attachment of the probe during labor due to the decreased risk of detachment caused by fetal and cervical forces.

It is to be understood that both the foregoing general description and the following detailed description are exemplary, but are not restrictive, of the invention

BRIEF DESCRIPTION OF THE DRAWINGS

The invention is best understood from the following detailed description when read in connection with the accompanying drawings, in which:

FIG. 1A is a cross-section of a non-invasive fetal probe having a shell coated with a non-conductive coating and gel constructed in accordance with the present invention with a brush-type fetal sensor;

FIG. 23 is a partial cross-section of an additional embodiment of a non-invasive fetal probe having low profile electrode leads; and FIGS. 24A, 24B, and 24C show cross-sectional, perspective, and top views, respectively, of an alternative fetal spring contact design.

DETAILED DESCRIPTION OF THE INVENTION

Figure 1B:
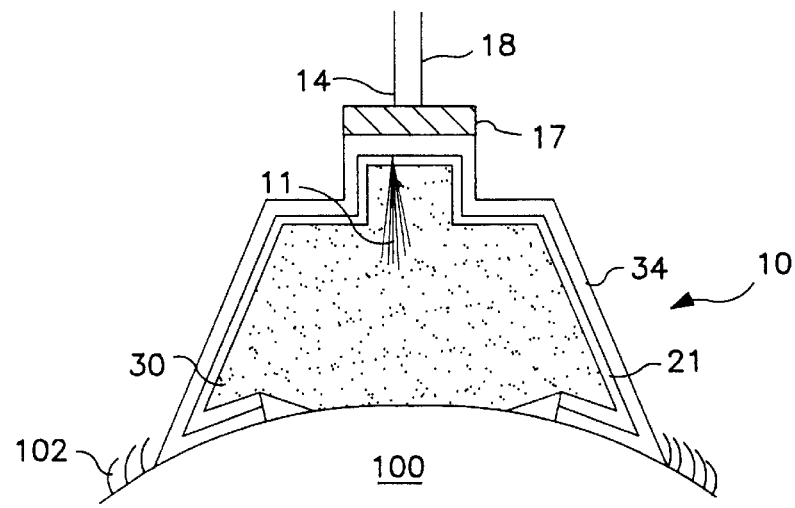
FIG. 1B is a cross-section of the non-invasive fetal probe shown in FIG. 1A attached to a fetus.

Referring now to the drawing, wherein like reference numerals refer to like elements throughout, FIGS. 1A, 1B, 2, 5, and 7–23 illustrate a non-invasive fetal probe 10 constructed in accordance with the present invention. It is emphasized that the reference numerals in this application correspond to like elements having the same reference numerals in the figures of U.S. Pat. No. 5,474,065. As used throughout the specification and claims, the words "carried by" define the structural relationship between specified elements as being established by attaching the elements to each other by either direct or indirect means. It is also emphasized that, according to common practice, the various elements of the drawing are not to scale. On the contrary, the width, length, and thickness of the various elements are arbitrarily expanded or reduced for clarity.

Fetal probe 10 is inserted through the birth canal and is attached to the presenting part (typically the head) of the fetus 100 as shown in FIG. 1B. Fetus 100 may have hair 102. Because it is "non-invasive," fetal probe 10 does not penetrate the fetal skin. Once attached, fetal probe 10 can continuously sense, depending upon the sensors incorporated in fetal probe 10, such fetal parameters as heart rate, blood gas composition, temperature, and pH levels during labor and delivery. These fetal parameters are received by monitor 80 as shown in FIG. 1A. Other types of sensors and test equipment or combinations of sensors and test equipment could be incorporated into fetal probe 10.

I. Non-invasive Fetal Probes Having Improved Electrical and Physical Properties

An important aspect of the present invention is the enhanced electrical and mechanical separation of the fetal and maternal sensors. Shown in FIGS. 1, 2, and 5–9 are non-invasive fetal probes having a polymer shell 34, preferably made of a thermoplastic polymer, coated with a gel 30 which is preferably a hydrogel having conductive and/or adhesive properties. The gel 30 may also be covered with an insulating barrier 21 to enhance the electrical isolation of the fetal sensor from electrical signals in the maternal environment. The insulating barrier 21 also provides enhanced electrical isolation between the fetal sensor 11 or 12 and the maternal sensor 16 or 17.

A. Non-invasive Fetal Probes Having Polymer Shells

Turning to FIGS. 1–8, fetal probe 10 has a fetal brush sensor 11 or fetal disk sensor 12 with an attached fetal connector 14. A maternal sensor 17 and attached maternal connector 18 may also be provided. Fetal sensors 11 or 12 and maternal sensor 17 are electrodes, and fetal connector 14 and maternal connector 18 are conductors, when fetal probe 10 is a fetal heart rate probe. Maternal sensor 17 can be positioned on the top surface of probe 10 or may extend down the sides of probe 10, so long as maternal sensor 17 does not contact the fetus to which probe 10 is adhered. Gel 30 provides the base to which fetal sensor 11, 12 and maternal sensor 17 are attached and secures fetal probe 10 to the presenting part of fetus 100.

Figure 6A:
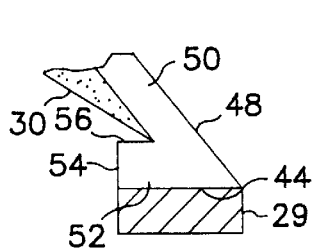
FIG. 6A is an exploded view of the ledge of the non-invasive fetal probe shown in FIG. 5.
Figure 6B:
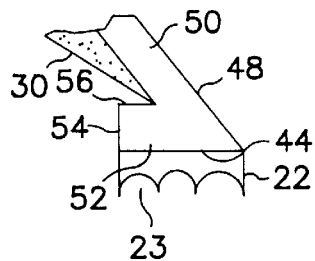
FIG. 6B is an exploded view of a modified ledge design incorporating a squeegee.
Figure 6C:
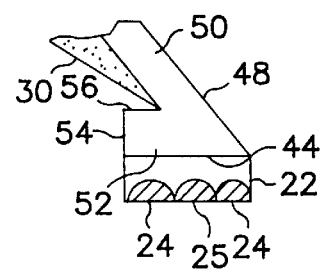
FIG. 6C is an exploded view of the design shown in FIG. 6B with additional coatings.
Figure 6D:
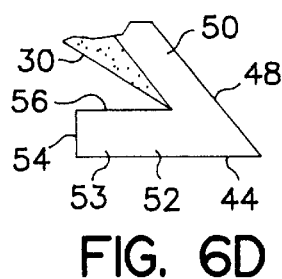
FIG. 6D shows an exploded view of an elongated ledge embodiment.
Figure 6E:
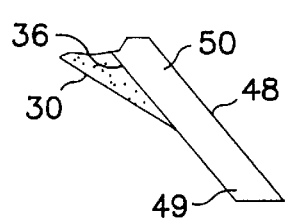
FIG. 6E shows an exploded view of an elongated shell embodiment.

Shell 34 can be formed by a number of processes understood by those skilled in the art, including molding. Suitable dimensions for shell 34 are a total height of about 6.2 mm and a diameter of about 15 mm. By using shell 34, the gel 30 and fetal sensor 11, 12 may be isolated from external fluids. FIGS. 6D and 6E show two variations in the configuration of wall 50 of shell 34.

FIG. 6D shows a ledge 52, which is a radially inward extension of the wall 50 in a plane which is approximately at a 30-degree angle to outer wall surface 48 of shell 34. A ledge extension 53 is provided which maximizes the electrical and physical separation between the fetal and maternal sensing elements. The angle of ledge 52 could be adjusted (for example, to angles between 15 and 60 degrees) to achieve a desired holding strength. Ledge 52 has a side surface 54; a bottom, horizontal surface 44; and a top surface 56.

Figure 6F:
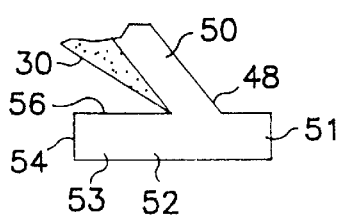
FIG. 6F shows an exploded view of an extended rim embodiment.
Figure 6G:
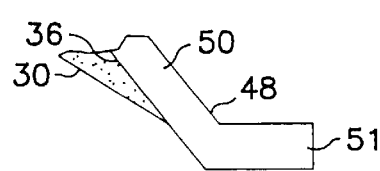
FIG. 6G shows an exploded view of an alternative extended rim embodiment.

FIG. 6G shows rim extension 51, which is a radially outward extension of the wall 50 in a plane which is approximately at a 30-degree angle to outer wall surface 48 of shell 34. The angle of rim extension 51 could be adjusted (for example, to angles between 15 and 60 degrees) to achieve a desired holding strength. FIG. 6F shows an embodiment having both a rim extension 51 and a ledge extension 53 used in combination which provides increased electrical and physical separation between the fetal and maternal sensing elements than that provided by either extension alone.

FIG. 6E shows a "straight" inner wall surface 36, without deviations or additions, entirely parallel to the outer wall surface 48 of wall 50 of shell 34. An outer wall extension 49 is provided which maximizes the electrical and physical separation between the fetal and maternal sensing elements.

As discussed above, by increasing the separation of the fetal and maternal sensors, the ledge extension 53 of FIG. 6D, outer wall extension 49 of FIG. 6E, rim extension 51 of FIG. 6G, when used alone or in combination, e.g., as in FIG. 6F, help to isolate the fetal sensor thereby allowing a monitor 80, as shown in FIG. 1A, to more easily isolate the fetal heart rate signal from maternal signals. The ledge extension 53, outer wall extension 49, and rim extension 51 further ensure the electrical isolation of the fetal and maternal sensors by forming a seal between the gel 30 and external fluids.

Figure 2:
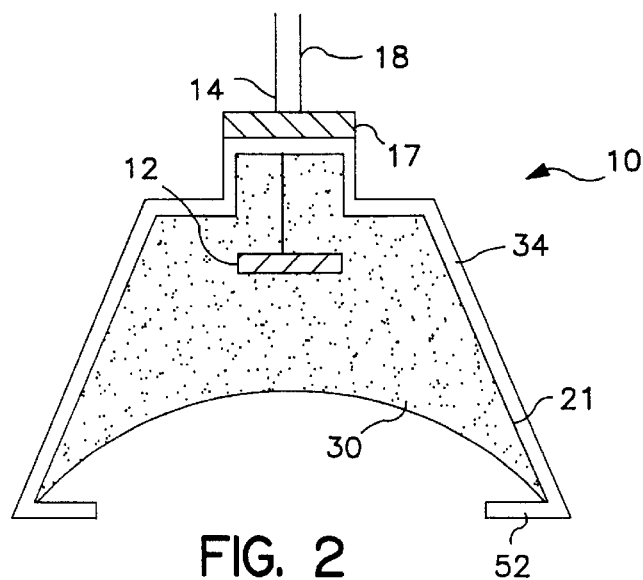
FIG. 2 is a cross-section of a non-invasive fetal probe having a shell coated with a gel constructed in accordance with the present invention with a fetal disk sensor.
Figure 3:
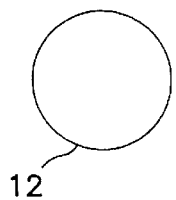
FIG. 3 is a planar view of the fetal disk sensor shown in FIG. 2.

As shown in FIG. 2, this increased separation may be provided by limiting the amount of gel 30 so that it does not extend completely to the edge of ledge 52 of polymer shell 34 which serves to insulate the gel 30 from the maternal sensor 17. Various thermoplastic resins are preferred materials for forming shell 34. Exemplary materials include Pellethane® resin (a polytetramethylene glycol ether resin available from Dow Chemical Company, such as Pellethane® 2363), Pebax® resin (a polyether block amide resin available from Atochem, Inc., such as Pebax® 2533), PVCs, polyurethanes, and polyethylenes. Each of these materials offer different combinations of characteristics important to the manufacture and operation of fetal probe 10. Some of these characteristics are ease of molding, strength, adhesion to gel compositions, hardness, water absorption, biocompatibility, price, and signal isolation.

Figure 5:
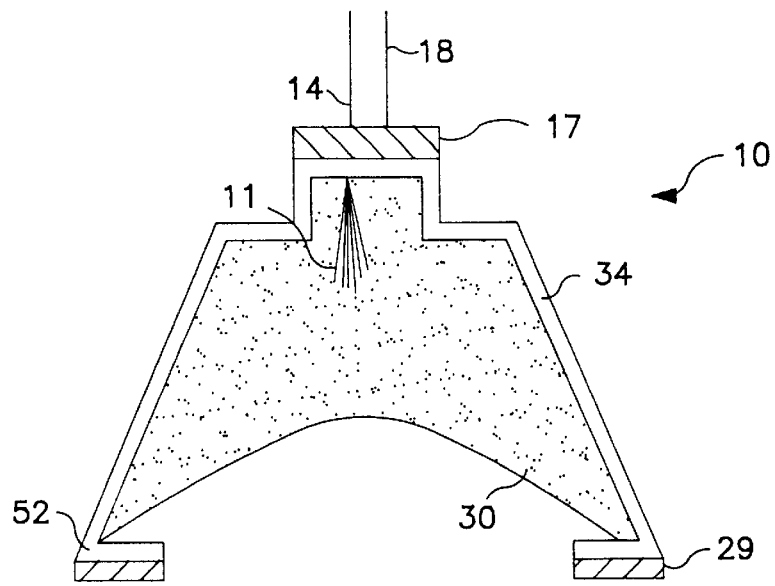
FIG. 5 is a cross-section of the non-invasive fetal probe having a ledge with a non-conductive coating.
Figure 7:
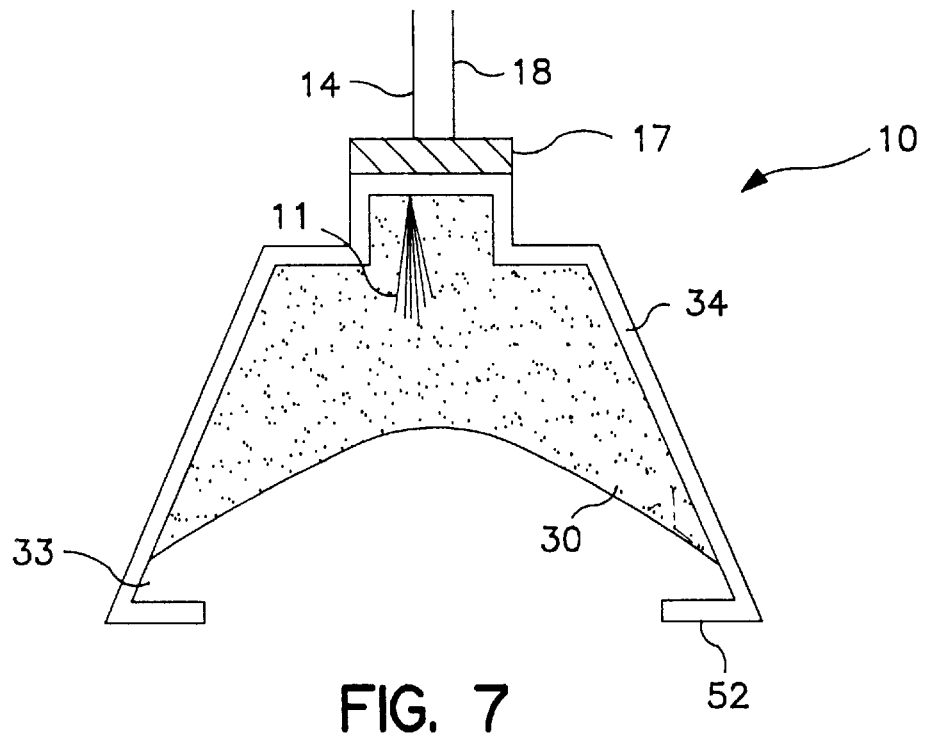
FIG. 7 is a cross-section of an additional embodiment of a non-invasive fetal probe having a shell coated with a gel, a ledge, and air gaps between the ledge and the gel.
Figure 8:
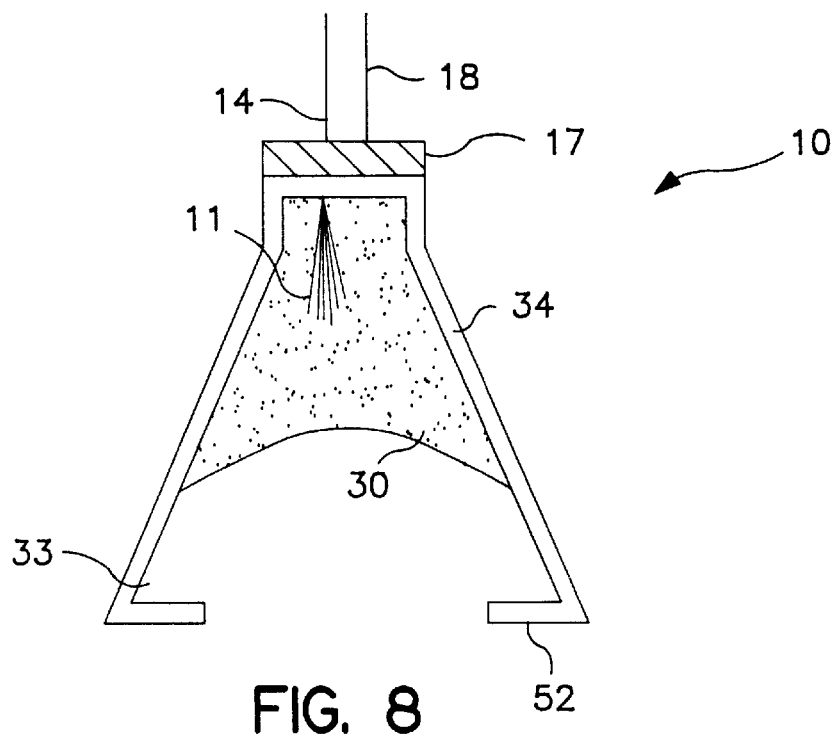
FIG. 8 is a cross-section of a non-invasive fetal probe having an air gap as shown in FIG. 7 but with a deeper, more-elongated shell.

Isolation of the fetal electrode from the maternal electrode may also be further enhanced by providing additional insulation which may be in the form of insulating barriers, non-conductive coatings, squeegees, and air gaps which are discussed below and may be used alone, in combination with one another, and in conjunction with the ledge extension 53 or outer wall extension 49 or rim extension 51. Shown in FIGS. 1A and 1B is an insulating barrier 21 which is disposed between shell 34 and gel 30. FIGS. 5 and 6A show a non-conductive coating 29 disposed on bottom surface 44 of ledge 52. FIGS. 6B and 6C show disposed on bottom surface 44 of ledge 52 a squeegee 22 having grooves 23 which may employ specially selected coatings such as an absorbant coating 24, a non-conductive adhesive coating 25, or both as shown, for example, in FIG. 6C. FIGS. 7 and 8 show an air gap 33 provided between ledge 52 and gel 30.

Figure 6H:
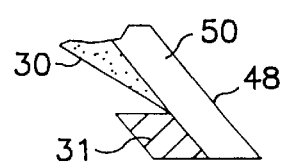
FIG. 6H shows an exploded view of a non-conductive rim embodiment.

In another embodiment, a non-conductive rim 31 is shown in FIG. 6H which helps to isolate the fetal sensor 11 from the maternal environment. The non-conductive rim 31 can be a non-conductive coating, preferably a non-conductive hydrogel adhesive coating The non-conductive rim 31 also helps in the attachment of the fetal probe 10 to a fetus having a particularly large amount of hair. This is accomplished by the ability of the non-conductive rim 31 to envelope fetal hair and, if a hydrogel adhesive is employed, through its wet adhesive properties. This non-conductive rim 31 is particularly useful when wall 50 of shell 34 has no ledge, rim, or other flange-like surface present to place against the fetal presenting surface. To further augment the physical separation between the maternal and fetal environments, a non-invasive fetal probe is provided as shown in FIG. 8. This embodiment of fetal probe 10 has a deeper, more elongated shell 34 in addition to air gap 33. This tapered design provides an increased path between and, thus, enhanced electrical separation of, the fetal sensor 11 and maternal sensor 17. The tapered design also has the advantage of providing a fetal probe 10 having a small enough diameter for ease of application early in labor. For example, a V-shaped concave cup with a diameter of 15 to 20 mm, or which can be collapsed into a dispenser or guide tube of this diameter or less, is preferred. Such a size permits application of fetal probe 10 when cervical dilation is 1 cm or less.

B. Non-invasive Fetal Probes with Non-conductive Rims

Figure 9:
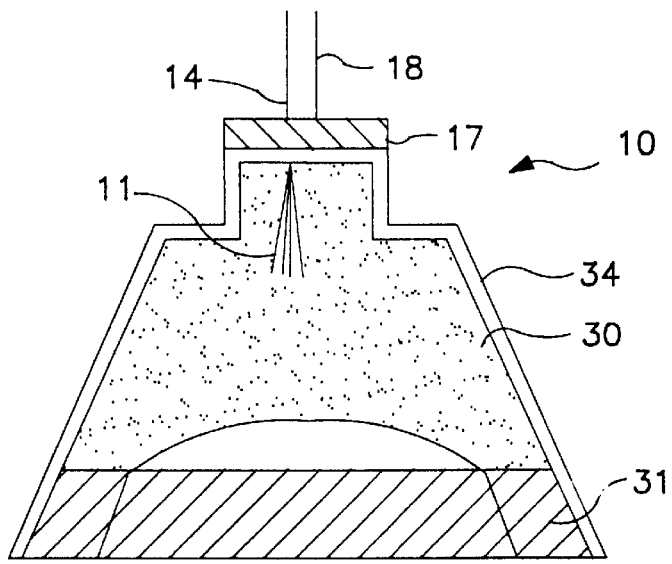
FIGS. 9–11 are cross-sections of non-invasive fetal probes having a conductive gel with non-conductive hydrogel adhesive coatings.
Figure 10:
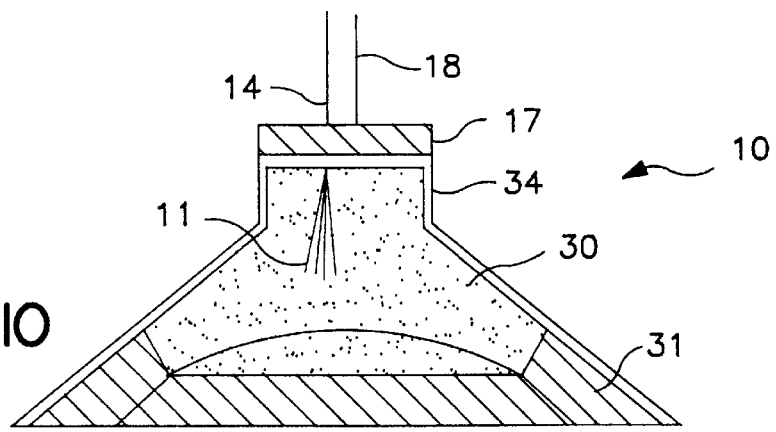
Figure 11:
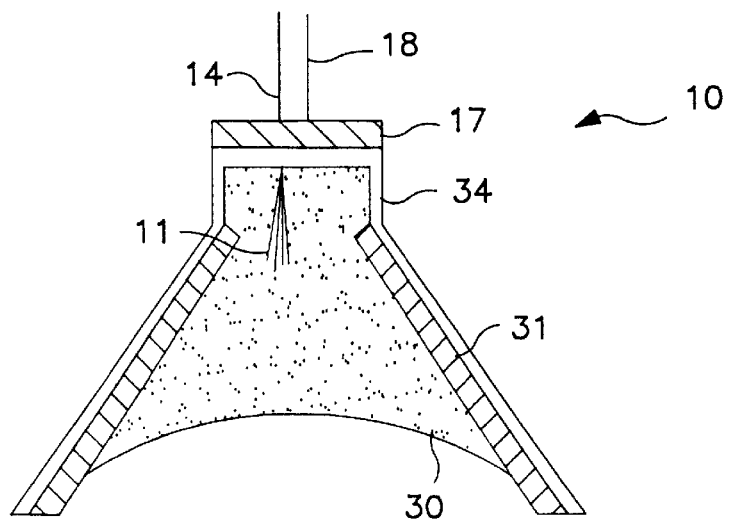

In an alternative embodiment, the non-invasive fetal probes according to the present invention can have gel 30 with a non-conductive rim 31. Shown in FIGS. 9–11 are fetal probes 10 having gel 30, which may be a conductive hydrogel, with a non-conductive rim 31 around the perimeter. The non-conductive rim 31 can be a non-conductive coating, preferably a non-conductive hydrogel adhesive coating, which helps to electrically isolate the fetal sensor 11, 12 from electrical signals in the maternal environment. The non-conductive rim 31 also helps to attach the fetal probe 10 to a fetus having a particularly large amount of hair. This is accomplished by the ability of the non-conductive rim 31 to envelope fetal hair and, if a hydrogel adhesive is employed, through its wet adhesive properties. This non-conductive rim 31 is particularly useful in isolating the fetal sensor 11, 12 from the maternal environment when no ledge, rim, or other flange-like surface is present to place against the fetal presenting surface.

Figure 12:
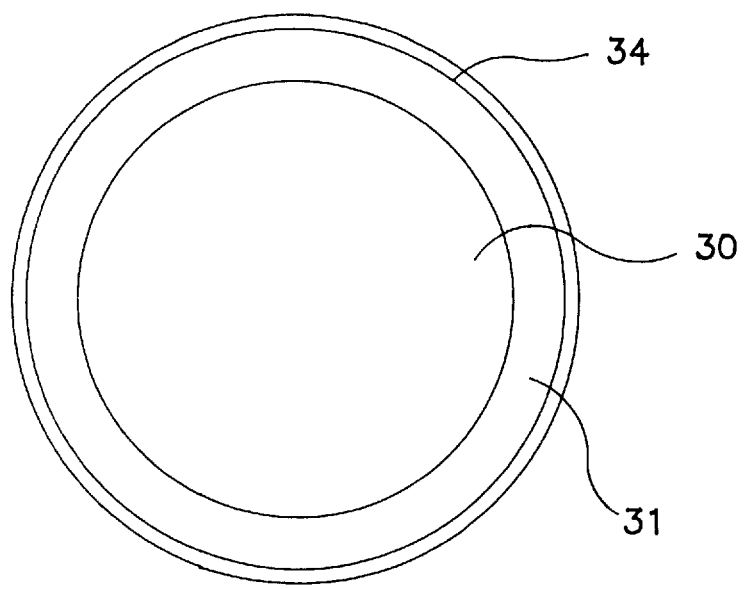
FIG. 12 is a bottom view of the non-invasive fetal probes of FIGS. 9–11.

Although FIGS. 9 and 10 show the non-conductive rim 31 extending only partially up from the fetal attachment surface, the non-conductive rim is not limited to this region but can extend further toward the maternal sensor 17 as shown in FIG. 11. FIG. 12 shows a bottom view of the fetal attachment surface of the probes 10 shown in FIGS. 9–11.

Figure 13:
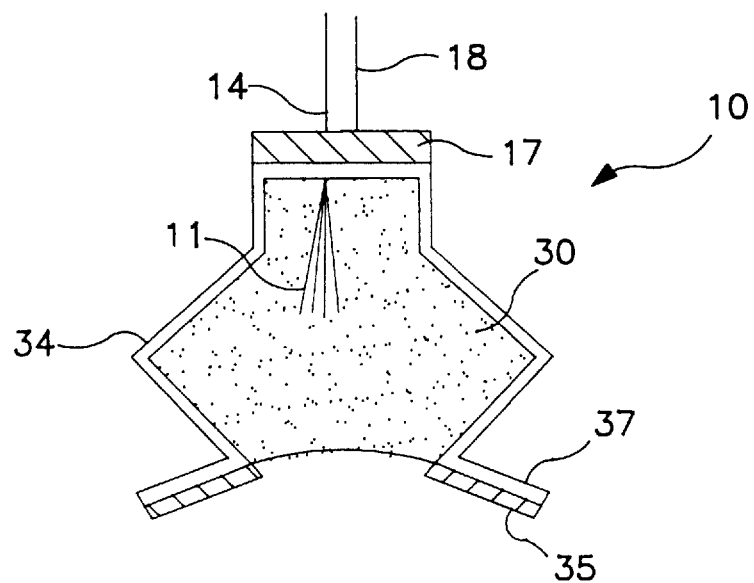
FIG. 13 shows another embodiment of the non-invasive fetal probe having a bellows-shaped gel construction.

In an additional embodiment, a non-invasive probe 10 having a shell extension configuration shown in FIG. 13 is provided which also maximizes the separation between the maternal and fetal environments. In this embodiment, gel 30 has a bellows configuration with a shell 34 and a shell extension 37 located around the perimeter of the fetal attachment surface which supports a non-conductive adhesive 35 which may be a hydrogel material.

As shown in FIGS. 9–13, fetal probe 10 is covered with a shell 34 and, in the embodiment shown in FIG. 13, an additional shell extension 37 which prevents the gel 30 from contacting the maternal environment in order to help electrically isolate the fetal sensor from electrical signals in the maternal environment. The shell 34 and shell extension 37 also provide electrical isolation between the fetal sensor 11, 12 and the maternal sensor 17.

II. Non-invasive Fetal Probes Having Low-profile Designs

In yet another embodiment, a non-invasive fetal probe having low-profile designs is provided as shown in FIGS. 20–23. In designing a fetal probe, consideration must be given to the attachment force which holds fetal probe 10 in place on a fetus. This attachment force must be sufficient to hold fetal probe 10 in place during labor which may require attachment times of ten hours or more. During labor a fetal probe is subjected to tipping forces which are generated by movement of the head of the fetus, the cervix of the mother, or both. The low-profile designs according to the present invention help decrease the tendency of the fetal probes to detach caused by these fetal and cervical forces generated upon the probe. This enables the non-invasive probe to be securely attached to the fetus during labor and delivery.

Figure 21:
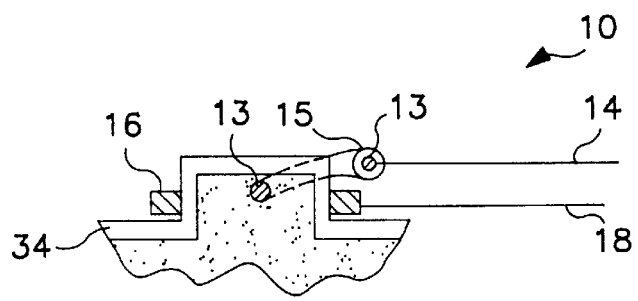
FIG. 21 is a partial cross-section of an additional embodiment of a non-invasive fetal probe having low profile electrode leads.
Figure 22:
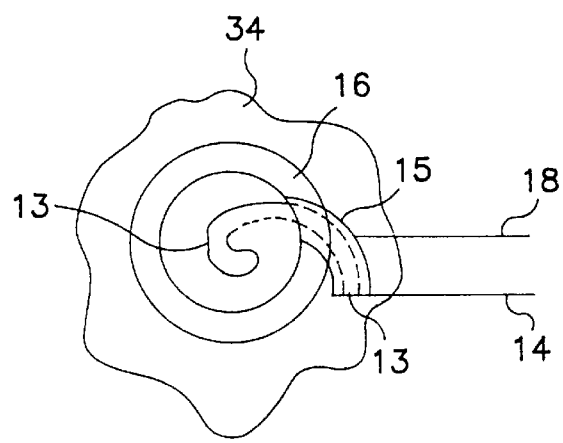
FIG. 22 is a top view of the non-invasive fetal probe shown in FIG. 21.

The fetal probe designs shown in FIGS. 20–23 achieve these low profiles by reducing the overall height of probe 10 by either forming fetal connector lead 14 and maternal connector lead 18 to include a substantially perpendicular bend (FIG. 20) or connecting these leads to the probe 10 in a radial direction (FIGS. 21 and 23). Where probe 10 incorporates shell 34, radial attachment of the fetal connector lead 14 can be accomplished by a fetal circumferential sensor 13 shown in FIGS. 21 and 22. The maternal sensor 16 of FIGS. 21 and 22 is preferably a steel band which is connected to maternal connector 18. In yet another embodiment, a fetal probe 10 having a low-profile is provided which has substantially flat fetal and maternal electrodes. A preferred embodiment, shown attached to fetus 100 in FIG. 23, is a fetal probe 10 having a maternal sensor 17 and a fetal sensor 12 both of which are flat disks and separated by insulating layer 19. Preferably, insulating layer 19 extends over fetal sensor 12 to enhance separation from maternal sensor 17.

III. Fetal Heart Rate Probe

One specific application of fetal probe 10 will be described to better illustrate the advantages of fetal probe 10. Fetal probe 10 may be used to monitor fetal heart rate without penetration of the fetal epidermis. At least four criteria affect the quality of the fetal heart rate signal monitored: (1) symmetry between the fetal and maternal (reference) electrodes, (2) maximum separation between the fetal and reference sensors, (3) maximum surface contact area to minimize impedance, and (4) stabilized connections. Application of fetal probe 10 to monitor fetal heart rate meets these criteria well.

In this application, a fetal sensor detects the electrical fetal heart rate signal transcutaneously. To do so, the fetal sensor must maintain contact with the presenting part of a fetus, either directly or through the gel 30. Preferably gel 30 is a conductive hydrogel in the case where electrical contact between the fetus and the fetal sensor is established indirectly through gel 30 as shown, for example, in FIGS. 1A, 1B, 2, 5, 7, 8, 9–11, and 13. In cases where the fetal sensor directly contacts the fetus, gel 30 may optionally include such a conductive material in order to enhance the electrical contact and transmission of electrical fetal signals. The fetal sensor itself must provide a sufficiently large surface area and be electrically conductive to sense the electrical fetal heart rate signal. The present invention includes various types of fetal sensors which are illustrative of, but not limited to, the types which may be employed. Discussed above are fetal brush sensor 11 (shown in FIGS. 1A, 1B, 5, 7–11, and 13) and fetal disk sensor 12 (shown in FIGS. 2, 3, and 23).

A suitable material for construction of fetal brush sensor 11 is multi-strand carbon fiber wire. Carbon wires are light weight, flexible, and radiolucent (i.e., they are partially or wholly transparent to X-Rays). Moreover, they provide good electrical conductivity and do not react with gel components or saline solutions. Suitable carbon wire can be obtained from Minnesota Wire and Cable Company in St. Paul, Minn. and can replace stainless steel in forming fetal sensor 11. Fetal brush sensors 11 could also be formed from multi-strand stainless steel wire, such as a Teflon®-coated steel wire sold by Cooner Wire in Chatsworth, Calif. Such wire is very fine and light weight; therefore, it adds little mass to fetal probe 10. When used to form fetal brush sensor 11, the Teflon® jacket is removed to expose the stainless steel wire. The exposed wires are then spread to form a brush. Alternative insulating jacket materials for the wire, other than Teflon®, could also be used.

Fetal circumferential sensor 13 can be formed from conductive wire (e.g., stainless steel) which does not react with gel components or saline solutions. The conductive wire used typically has an isolating jacket 15 which protects the wire portion of the fetal circumferential sensor 13 extending outside of shell 34 from the maternal environment. See FIGS. 21 and 22. The isolating jacket 15 is stripped to expose the wire portion of the fetal circumferential sensor 13 on the inside of shell 34 so that it may contact the conductive gel 30.

Figure 17:
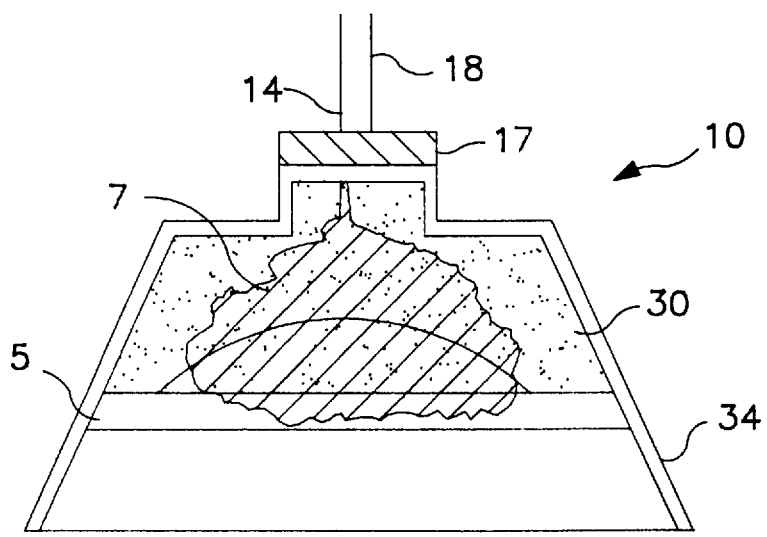
FIG. 17 is a cross-section of the non-invasive fetal probe of FIG. 16 with an additional adhesion-promoting surface on the gel.
Figure 18:
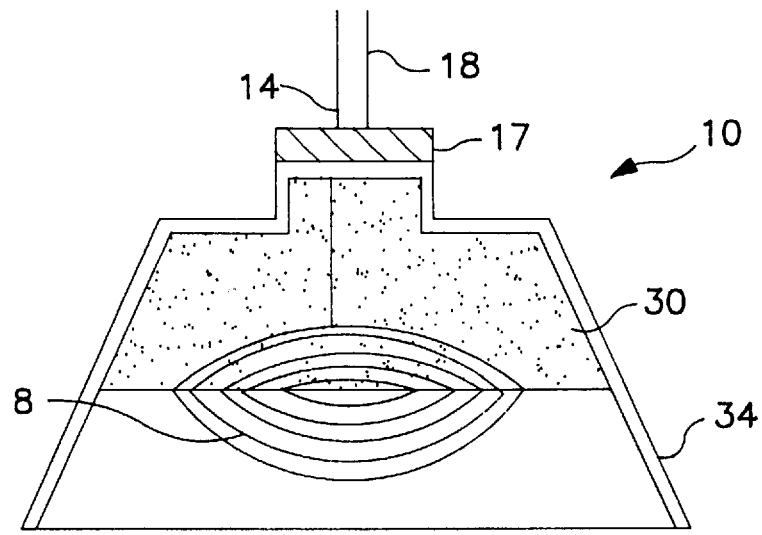
FIG. 18 is a cross-section of a non-invasive fetal probe having a shell coated with a gel having a fan-strand fetal sensor.
Figure 19:
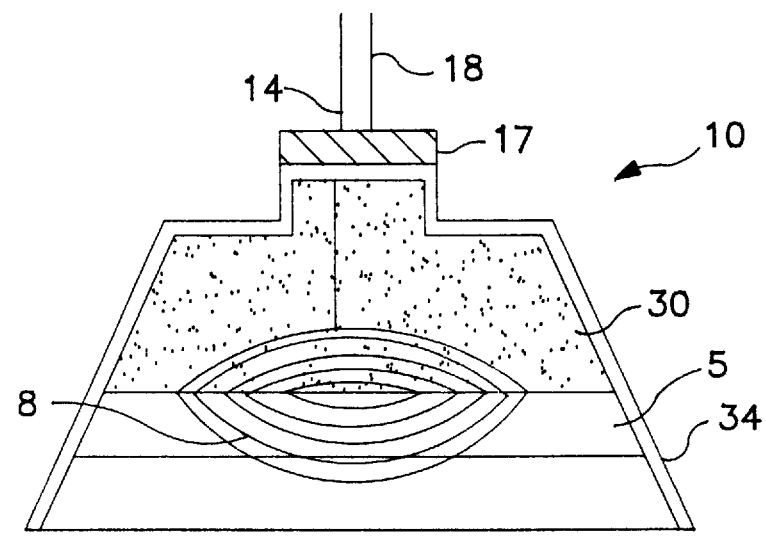
FIG. 19 is a cross-section of the non-invasive fetal probe of FIG. 18 with an additional adhesion-promoting surface on the gel.
Figure 20:
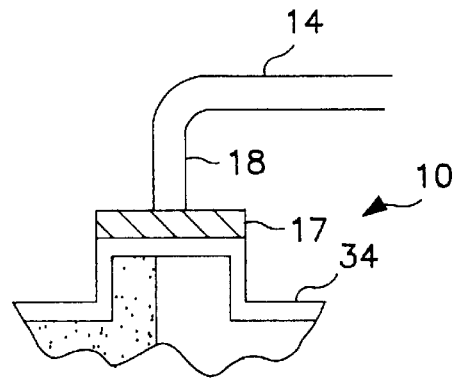
FIG. 20 is a partial cross-section of an additional embodiment of a non-invasive fetal probe having low profile electrode leads.

Fetal disk sensor 12 in this application can be the silver-silver chloride sensor commonly used in ECG monitoring electrodes. Additional fetal sensors are also provided which are useful in the present invention, namely, a loop array 6 (FIGS. 14–15), a conductive fiber "wool" or mesh 7 (FIGS. 16–17), and a conductive "fan strand" configuration 8 (FIGS. 18–19). The materials used for these various fetal sensors should be conductive and unreactive with gel components or saline solutions. Furthermore, the materials incorporated in fetal sensors should also not react with the fetal tissue or in the fetal environment (e.g., with the vernix or meconium). Although not intending to be limited to any particular materials selection, exemplary materials particularly useful for the fetal sensors of the present invention are carbon fibers, stainless steel, silver, gold, silver-silver chloride, and combinations thereof.

It is envisioned and understood that the various fetal sensors are interchangeable with and can be incorporated either in place of or in combination with any of the fetal sensors of the non-invasive probes disclosed (the probes themselves are merely exemplary of the present invention). Unless otherwise specified, hereinafter the term "fetal sensor" collectively refers to fetal brush 11, fetal disk 12, fetal circumferential sensor 13, loop array 6, conductive fiber "wool" or mesh 7, and conductive "fan strand" 8 configurations.

Figure 14:
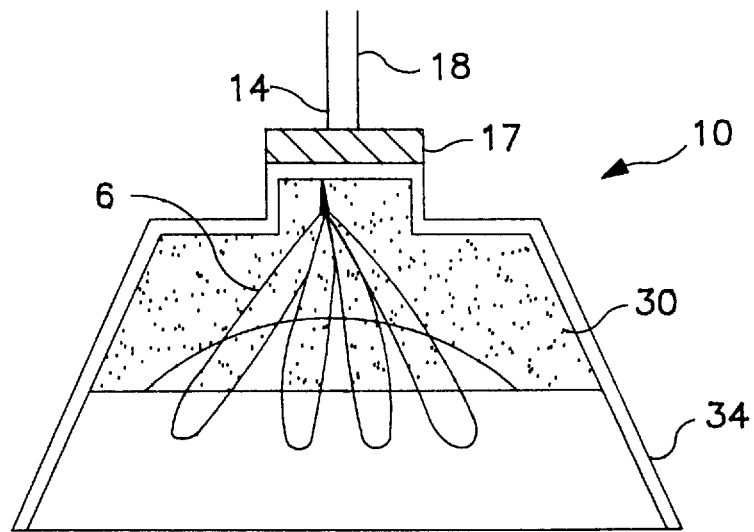
FIG. 14 is a cross-section of a non-invasive fetal probe having a shell coated with a gel having a loop-array fetal sensor.
Figure 15:
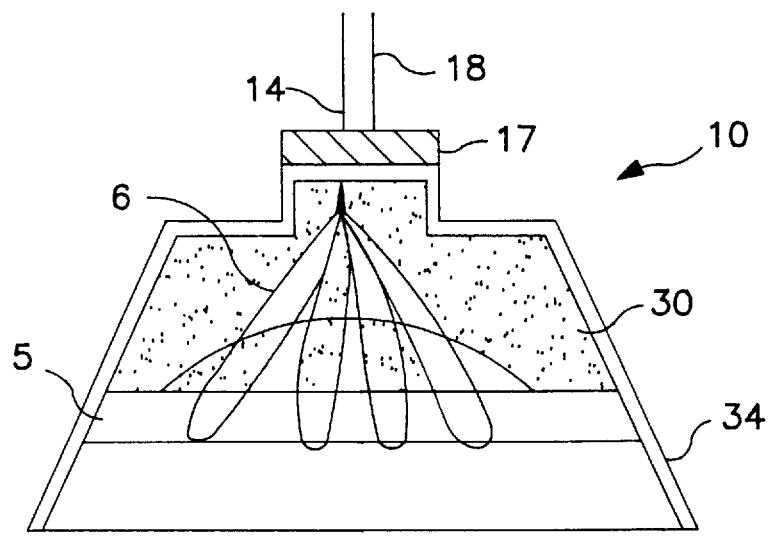
FIG. 15 is a cross-section of the non-invasive fetal probe of FIG. 14 with an additional adhesion-promoting surface on the gel.
Figure 16:
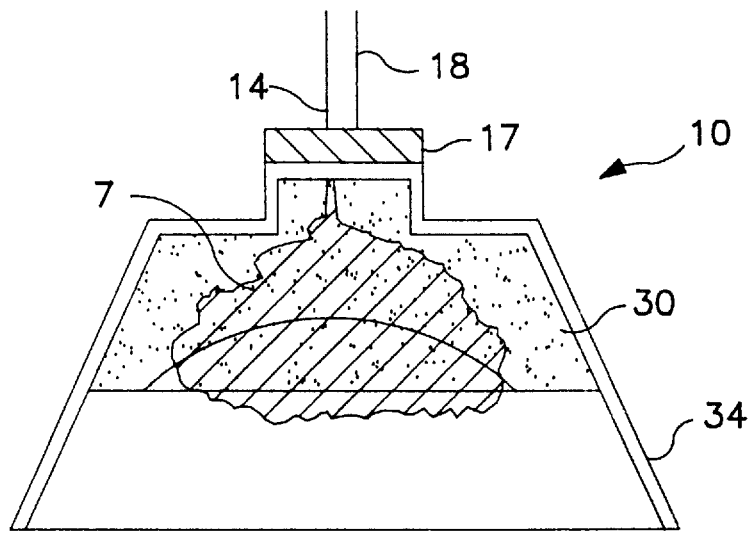
FIG. 16 is a cross-section of a non-invasive fetal probe having a shell coated with a gel having a conductive wool or conductive mesh fetal sensor.

The fetal sensors shown in FIGS. 14, 16, and 18 are shown partially embedded in and partially protruding out of gel 30 in order to provide direct contact, and thus enhance conductivity, between the fetal sensor and the fetal tissue when the fetal probe is attached to the presenting part of the fetus. When the partially embedded fetal sensors of FIGS. 14, 16, and 18 are used to establish direct contact with a fetus, the fetal sensors may also be covered with an adhesion-promoting layer 5 as shown in FIGS. 15, 17, and 19. The adhesion-promoting layer 5 can include a lubricating jelly (e.g., K-Y® jelly) or a conductive medium (e.g., a conductive migrating hydrogel) which can flow around hair to improve adhesion. In the case of the conductive migrating hydrogel, the additional advantage of lower impedance at the skin-sensor interface is also realized.

Additional means are also provided for increasing the fetal and maternal differential signals. This is achieved by spring contact 58 shown in FIG. 24A which is partially embedded in gel 30 and provides for direct contact, and thus enhanced conductivity, between the fetal sensor and the fetal tissue when the fetal probe is attached to the presenting part of the fetus. Spring contact 58 is shown in a perspective view in FIG. 24B and in a top view in FIG. 24C.

In this application, fetal connector 14 is an insulated lead wire suitable for conducting the electrical signals from the fetal sensor to a monitoring signal-processing unit without being susceptible to interference from the maternal environment and maternal sensor. Fetal connector 14 passes through shell 34 into gel 30 and maternal sensor 16 or 17 and is ultimately connected (perhaps through other wires and electrical connections) to a fetal heart rate monitor 80 shown in FIG. 1A. The environment in which fetal probe 10 is used, namely inside the uterus, requires insulation of the lead wire. The connection between fetal connector 14 and fetal sensor 12 is embedded in the gel 30.

The fetal sensors of the present invention may be entirely embedded in gel 30 (as shown in FIGS. 1A, 1B, 2, 5, 7–11, and 13), partially embedded in or positioned on the surface of gel 30 (as shown in FIGS. 14, 16, and 18) or otherwise carried by gel 30. In the case that the fetal sensors are not entirely embedded in the gel 30, if an adhesion promoting layer 5 is used, the fetal sensors of the present invention may also be either partially (FIGS. 15 and 19) or totally (FIG. 17) embedded in the adhesion-promoting layer 5. In any case, fetal sensor connector 14 and maternal sensor connector 18 connect the fetal and maternal sensors, respectively, to an external monitor 80.

In this application, maternal sensors 16 and 17 must provide a sufficiently large surface area and be electrically conductive to sense the electrical maternal heart rate signal and other muscular or electrical activity. In addition, maternal sensors 16 and 17 must be inert to chemical reaction with biological fluids and tissues. Multi-strand stainless steel or carbon fiber wires, described above for use as fetal sensor 11, can also be used for maternal sensor 16. Alternatively, maternal sensor 16 may be an electrically conducting material such as a metal foil (e.g., silver, aluminum, or stainless steel) or metallized film (e.g., aluminum metallized polyester) which covers the upper surface of insulating barrier 21. Other electrically conductive, non-metallic films and coatings such as conductive carbon and conductive graphite may also be used.

Figure 4A:
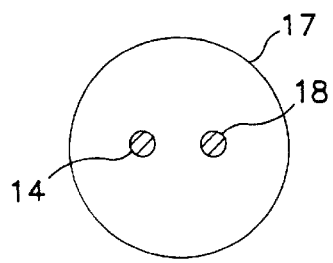
FIG. 4A is a planar view of a maternal disk sensor.
Figure 4B:
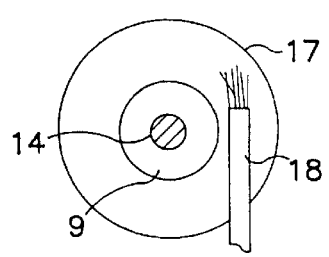
FIG. 4B is a planar view of an alternative maternal disk sensor.

Maternal sensor 16 (FIGS. 21 and 22) and maternal sensor 17 (FIGS. 1, 2, 4, 5, 7–11, 13–20, and 23) may be a band, washer, wire loop, or plate which fits on top of or is otherwise carried by shell 34 or insulating layer 19. In an exemplary embodiment, as shown in FIGS. 4A and 4B, stainless steel disk 17 can be approximately 3.5 to 4.0 mm wide (preferably 3.7 mm) and 5.0 to 5.5 mm in diameter (preferably 5.4 mm) and may contain an enlarged hole 9 (FIG. 4B) to facilitate passage of the fetal connector 14 therethrough. Maternal connector 18 is a lead wire which can be a sheathed multi-strand wire connected to maternal sensor 17 for communicating received electrical signals. Maternal connector 18 can be attached perpendicular to (FIG. 4A) or in the plane of maternal sensor 17. Typically, the wire(s) of maternal connector 18 is (are) attached to maternal sensor 17 by a spot welding operation.

Maternal sensors 16 and 17 detect primarily the maternal electrical environment while fetal sensors 11, 12, and 13 detect primarily the fetal electrical environment on the surface of the fetus. The signal received by each sensor, however, has a minor component signal from the other environment (i.e., the fetal sensor detects signals from the maternal environment while the maternal sensor detects signals from the fetus). By using the signal detected by maternal sensors 16 and 17 as a reference signal, any maternal heart signals and other muscular or electrical signals which pass through the fetus and are detected by the fetal sensor can be filtered electronically in the fetal monitor 80 to provide a differential signal which is an accurate fetal heart rate measurement. This is accomplished by isolating the fetal R-waves from the other signals.

Non-invasive fetal probe 10 has two leads 14, 18—similar to conventional fetal scalp electrodes—for the fetal sensor and maternal sensor. Both the fetal and maternal leads 14 and 18 could be replaced by a non-wired connecting system, such as a radio transmission system, to communicate information from the fetal sensor and maternal sensors 16 or 17 to monitor 80. A radio system would require supporting hardware as is understood by those skilled in the art.

Referring back to insulating barrier 21 (FIGS. 1A, 1B, and 2) and non-conductive coating 29 (FIGS. 5 and 6A), these elements serve to maintain electrical insulation between the fetal and maternal sensors. Pebax®, a polyether block amide, is one type of insulating material which can be incorporated to serve this purpose. Other similar materials having sufficiently high dielectric properties also would suffice. Insulating barrier 21 and non-conductive coating 29 should be flexible so as not to impede the flexibility of gel 30.

With respect to non-conductive coating 29 (FIGS. 5 and 6A), non-conductive adhesive 35 (FIG. 13), and adhesion-promoting layer 5 (FIGS. 15, 17, and 19), because these elements contact the fetus, they preferably incorporate adhesive materials which are conformable and used in amounts and in thicknesses sufficient to envelop fetal hair and other surface irregularities and to promote attachment to a fetus having a large amount of hair. In addition to promoting attachment to fetal tissue, the adhesive materials used should be capable of enhancing the electrical isolation of the fetal probe from the maternal environment. An adhesive with "wet" tack capabilities is particularly preferred.

Selection of the gel compositions and production techniques useful in the present invention is within the purview of those skilled in the art, with examples being given, but not limited to, the hydrogels in U.S. Pat. No. 5,474,065. The hydrogel compositions disclosed therein can be molded or formed to provide almost any desired size and shape. Gel 30 can be formed by dispensing the gel composition into a mold of the desired shape then polymerizing the monomers of the gel in the mold. Alternatively, suction cup-shaped probes can be prepared by spin casting, similar to the procedure used to prepare soft contact lenses. Although conductive gels are preferred for constructing gel 30 in order to enhance or establish electrical contact between the fetal sensor and the presenting part of the fetus, it is recognized that gel 30 need not be a conductive material in cases where the fetal sensor establishes direct contact with the fetus.

Although illustrated and described herein with reference to certain specific embodiments, the present invention is nevertheless not intended to be limited to the details shown. It is understood that the various embodiments are merely illustrative of the present invention and that the various features may be used alone or in conjunction with one another in any combination as will be readily recognized by those having ordinary skill in the art.

It is also recognized that various modifications may be made in the details within the scope and range of equivalents of the claims and without departing from the spirit of the invention. For example, although the fetal probe 10 of the present invention has been described in detail for attachment of non-invasive fetal heart rate sensors, fetal probe 10 could also be used for other sensors such as blood gas analyzers and oximetry sensors. If so, fetal connector 14 and maternal connector 18 may constitute fiber optics rather than lead wires.

What is claimed:

1. A non-invasive fetal probe adapted for attachment to the presenting part of a fetus and monitoring at least one fetal parameter during labor and delivery, said probe comprising:

a shell having a non-conductive element;

a gel coated on said shell forming a surface for securing the probe to a fetus to be monitored, a fetal sensor carried by said gel for detecting at least one fetal parameter, said non-conductive element of said shell isolating said fetal sensor from fluids in an environment surrounding the probe;

a maternal sensor carried by said shell for detecting at least one maternal parameter; and means for communicating the fetal and maternal parameters detected by said fetal sensor and said maternal sensor, respectively, to a monitor.

2. A non-invasive fetal probe as recited in claim 1 wherein said non-conductive element is selected from the group consisting of a non-conductive rim, a ledge, a wall extension, a rim extension, and combinations thereof.

3. A non-invasive fetal probe as recited in claim 2 further comprising an insulating barrier disposed between said shell and said gel.

4. A non-invasive fetal probe as recited in claim 2 wherein said shell is a polymer.

5. A non-invasive fetal probe as recited in claim 2 wherein said non-conductive element is a ledge having a side surface, a top surface, and a bottom surface, said probe further comprising an air gap disposed between said top surface of said ledge and said surface formed by said gel.

6. A non-invasive fetal probe as recited in claim 5 wherein said gel is "V"-shaped.

7. A non-invasive fetal probe as recited in claim 6 wherein said gel has a diameter of 10–20 mm.

8. A non-invasive fetal probe as recited in claim 2 wherein said non-conductive element is a wall extension extending from said shell beyond said surface formed by said gel.

9. A non-invasive fetal probe as recited in claim 2 wherein said fetal sensor is selected from the group consisting of a brush sensor, a disk sensor, a loop array, a conductive fiber wool, a conductive fiber mesh, a conductive fan strand, and combinations thereof.

10. A non-invasive fetal probe as recited in claim 9 wherein said fetal sensor comprises at least one material selected from the group consisting of carbon fibers, stainless steel, silver, gold, silver-silver chloride, and combinations thereof.

11. A non-invasive fetal probe as recited in claim 9 further comprising an adhesion-promoting layer disposed on said fetal sensor.

12. A non-invasive fetal probe as recited in claim 11 wherein said adhesion-promoting layer comprises at least one material selected from the group consisting of a lubricating jelly, a conductive medium, a conductive migrating hydrogel, and combinations thereof.

13. A non-invasive fetal probe as recited in claim 2 wherein said means for communicating comprises a fetal connector connecting said fetal sensor to said monitor and a maternal connector connecting said maternal sensor to said monitor.

14. A non-invasive fetal probe as recited in claim 13 wherein said fetal connector and said maternal connector extend in a radial direction from said shell and each comprise a substantially perpendicular bend.

15. A non-invasive fetal probe as recited in claim 13 wherein said fetal connector and said maternal connector extend in a radial direction from said shell.

16. A non-invasive fetal probe as recited in claim 15 wherein said fetal sensor is a fetal circumferential sensor and said fetal connector is connected to said fetal circumferential sensor.

17. A non-invasive fetal probe as recited in claim 2 wherein said gel further comprises a partially embedded spring contact means adapted for directly contacting the fetus to be monitored upon securing said gel to the presenting part.

18. A non-invasive fetal probe as recited in claim 2 wherein said non-conductive rim is a non-conductive hydrogel adhesive coating formed on said shell.

19. A non-invasive fetal probe as recited in claim 1 wherein said gel is a conductive hydrogel.

20. A non-invasive fetal probe as recited in claim 1 wherein said gel is an adhesive hydrogel.

21. A non-invasive fetal probe as recited in claim 1 wherein said gel is a conductive adhesive hydrogel.

22. A non-invasive fetal probe adapted for attachment to the presenting part of a fetus and monitoring at least one fetal parameter during labor and delivery, said probe comprising:
   a shell;
   a gel coated on said shell forming a surface for securing the probe to a fetus to be monitored, said shell having an outer perimeter forming a ledge with a side surface, a top surface, and a bottom surface which isolates said gel from fluids in an environment surrounding the probe;
   a fetal sensor carried by said gel for detecting at least one fetal parameter; and
   an insulating element disposed on said bottom surface of said ledge.

23. A non-invasive fetal probe as recited in claim 22 wherein said insulating element is a non-conductive coating disposed on said bottom surface of said ledge.

24. A non-invasive fetal probe as recited in claim 22 wherein said insulating element is a squeegee having grooves.

25. A non-invasive fetal probe as recited in claim 24 further comprising at least one coating selected from the group consisting of an absorbant coating, a non-conductive adhesive coating, and combinations thereof disposed in said grooves.

26. A non-invasive fetal probe as recited in claim 22 wherein said gel is a conductive hydrogel.

27. A non-invasive fetal probe as recited in claim 22 wherein said gel is an adhesive hydrogel.

28. A non-invasive fetal probe as recited in claim 22 wherein said gel is a conductive adhesive hydrogel.

29. A non-invasive fetal probe attaching to the presenting part of a fetus and monitoring at least one fetal parameter during labor and delivery, said probe comprising:
   a gel forming a surface which secures the probe to a fetus to be monitored and has an outer perimeter with a non-conductive rim disposed thereon;
   a shell disposed on said gel;
   a fetal sensor carried by said gel for detecting at least one fetal parameter; and
   means for communicating the fetal parameter detected by said sensor from said sensor to a monitor.

30. A non-invasive fetal probe as recited in claim 29 wherein said non-conductive rim is a non-conductive hydrogel adhesive coating disposed on said outer perimeter of said surface of said gel.

31. A non-invasive fetal probe as recited in claim 29 wherein said gel is bellows-shaped and said non-conductive rim is a non-conductive adhesive supported by a shell disposed on said outer perimeter of said gel.

32. A non-invasive fetal probe as recited in claim 29 wherein said gel is a conductive hydrogel.

33. A non-invasive fetal probe as recited in claim 29 wherein said gel is an adhesive hydrogel.

34. A non-invasive fetal probe as recited in claim 29 wherein said gel is a conductive adhesive hydrogel.

35. A non-invasive fetal probe adapted for attachment to the presenting part of a fetus and monitoring at least one fetal parameter during labor and delivery, said probe comprising:

a substantially flat gel carrying a fetal sensor for detecting at least one fetal parameter, said gel having a surface for securing the probe to a fetus to be monitored;

a substantially flat insulating layer disposed on said gel;

a substantially flat maternal sensor carried by said insulating layer for detecting at least one maternal parameter; and means for communicating the fetal and maternal parameters comprising a fetal connector connecting said fetal sensor to said monitor and a maternal connector connecting said maternal sensor to said monitor, wherein said fetal connector and said maternal connector extend in a radial direction from said gel.

36. A non-invasive fetal probe as recited in claim 35 wherein said gel is a conductive hydrogel.

37. A non-invasive fetal probe as recited in claim 35 wherein said gel is an adhesive hydrogel.

38. A non-invasive fetal probe as recited in claim 35 wherein said gel is a conductive adhesive hydrogel.

* * * * *